United States Patent
Singh

(10) Patent No.: US 7,198,919 B1
(45) Date of Patent: Apr. 3, 2007

(54) USE OF ALPHA FACTOR SEQUENCES IN YEAST EXPRESSION SYSTEMS

(75) Inventor: Arjun Singh, Pacifica, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 08/448,946

(22) Filed: May 24, 1995

Related U.S. Application Data

(63) Continuation of application No. 07/552,719, filed on Jul. 16, 1990, now abandoned, which is a continuation of application No. 06/506,098, filed on Jun. 20, 1983, now abandoned, and a continuation-in-part of application No. 06/488,323, filed on Apr. 25, 1983, now abandoned.

(51) Int. Cl.
*C12P 21/02* (2006.01)
*C12N 1/19* (2006.01)
*C12N 15/81* (2006.01)

(52) U.S. Cl. .............. 435/69.51; 435/69.1; 435/69.6; 435/69.9; 435/254.2; 435/320.1

(58) Field of Classification Search ............. 435/69.1, 435/67.7, 172.3, 320.1, 69.9, 254.2
See application file for complete search history.

(56) References Cited

U.S. PATENT DOCUMENTS

| | | | | |
|---|---|---|---|---|
| 4,411,994 | A | | 10/1983 | Gilbert et al. ............ 435/69.7 |
| 4,546,082 | A | * | 10/1985 | Kurjan et al. ............ 435/172.3 |
| 4,762,791 | A | * | 8/1988 | Goeddel et al. ............ 435/243 |
| 4,775,622 | A | | 10/1988 | Hitzeman et al. ............ 435/69.4 |
| 4,870,008 | A | | 9/1989 | Brake ............ 435/69.4 |
| 4,914,026 | A | * | 4/1990 | Brake et al. ............ 435/69.4 |

FOREIGN PATENT DOCUMENTS

| | | |
|---|---|---|
| EP | 060057 | 9/1982 |
| EP | 116201 | 8/1984 |
| EP | 121884 | 10/1984 |
| EP | 123228 | 10/1984 |
| EP | 123289 | 10/1984 |
| EP | 123294 | 10/1984 |
| EP | 128733 | 12/1984 |
| EP | 129073 | 12/1984 |
| WO | WO 85/02200 | 5/1985 |
| WO | WO 85/04870 | 11/1985 |

OTHER PUBLICATIONS

Bitter et al., "Secretion of foreign proteins from *Saccharomyces cerevisiae* directed by α-factor gene fusions" *Proc. Natl. Acad. Sci. USA* 81:5330-5334 (1984).
Brake et al, "α-Factor-directed synthesis and secretion of mature foreign proteins in *Saccharomyces cerevisiae*" *Proc. Natl. Acad. Sci* 81:4642-4646 (1984).
Brake et al., "A functional prepro-α-factor gene in saccharomyces yeasts can contain three, four, or five repeats of the mature pheromone sequence" *Molec. and Cell. Biol.* 3(8):1440-1450 (1983).
Brake et al., "Identification and Characterization of a Structural Gene for the Yeast Peptide Mating Pheromone, a-factor" *J. Cell. Biochem.* (abstract 1497) Supp. 7B (Apr. 29, 1983).
Broach et al., "Transformation in yeast: development of a hybrid cloning vector and isolation of the cani gene" *Gene* 8:121-133 (1979).
Davis and Tai, "The mechanism of protein secretion across membranes" *Nature* 283:433-438 (1980).
Emr et al., "An MFα1-SUC2 (α-factor-invertase) gene fusion for study of protein localization and gene expression in yeast" *Proc. Natl. Acad. Sci. USA* 80:7080-7084 (Dec. 1983).
Hitzeman et al., "Expression of a Human Gene for Interferon in Yeast" *Nature* 293:717-722 (1981).
Hitzeman et al., "Secretion of human interferons by yeast" *Science* 219:620-625 (1983).
Hollenberg, C., "Cloning with 2-μm DNA vectors and the expression of foreign genes in *Saccharomyces cerevisiae*" *Current Topics in Microbiology and Immunology* 96:119-144 (1982).
Kurjan et al., "Structure of a yeast pheromone gene (MFα): a putative α-factor precursor contains four tandem copies of mature α-factor" *Cell* 30:933-943 (1982).
Miyanohara et al., "Expression of hepatitis B surface antigen gene in yeast" *Proc. Natl. Acad. Sci. USA* 80:1-5 (1983).
Palva et al., "Secretion of interferon by bacillus subtilis" *Gene* 22:229-235 (1983).
Rinderknecht and Humbel, "The amino acid sequence of human insulin-like growth factor I and its structural homology with proinsulin" *Journal of Biological Chemistry* 253(8):2769-2776 (1978).

(Continued)

*Primary Examiner*—Robert A. Wax
(74) *Attorney, Agent, or Firm*—Sharon E. Crane; Bingham McCutchen, LLP

(57) ABSTRACT

The isolation of the yeast α-factor genes is described. The promoter and signal peptide portions are isolated and joined to DNA coding for proteins heterologous to yeast in a plasmid which is used to transform yeast cells. The yeast expresses the heterologous DNA and processes and secretes the heterologous protein.

7 Claims, 12 Drawing Sheets

OTHER PUBLICATIONS

Roggenkamp et al., "Expression and processing of bacterial β-lactamase in the yeast *Saccharomyces cerevisiae*" *Proc. Natl. Acad. Sci USA* 78 (7) :4466-4470 (1981).

Singh et al., "*Saccharomyces cerevisiae* contains two discrete genes coding for the α-factor pheromone" *Nucleic Acids Research* 11 (12) :4049-4063 (1983).

Singh et al., "Synthesis, secretion and procession of α-factor-interferon fusion proteins in yeast" *Nucleic Acids Research* 12 (23) :8927-8938 (1984).

Thorner, "Pheromone Biosynthesis" *The Molecular Biology of the Yeast Saccharomyces*, Strathern et al., eds. pp. 161-163 (1981).

Tuite et al., "Regulated high efficiency expression of human interferon-α in *Saccharomyces cerevisiae*" *EMBO Journal* 1 (5) :603-608 (1982).

Weck et al., "Antiviral activities of hybrids of two major human leukocyte interferons" *Nucleic Acids Research* 9 (22) :6153-6166 (1981).

Zsebo et al., "Protein secretion from *Saccharomyces cerevisiae* directed by the prepo-α-factor leader region" *Journal of Biological Chemistry* 261 (13) :5858-5865 (1986).

Mullenbach et al. *Amer. Soc. Biol. Chemists. 74th Annual Meeting*, San Francisco, CA (Poster Jun. 5, 1983).

Mullenbach et al., "The Chemical Synthesis, Molecular Cloning and Expression in Yeast of Genes Coding for Human Insulin-Like Growth Factors" *Federation Proceedings* (AB#434) 42 (7) :1832 (May 1, 1983).

\* cited by examiner

| Carboxy terminus of α-factor: | Gly — | Gln — | Pro — | Met — | Tyr COOH |
|---|---|---|---|---|---|
| Possible codons and their usage | GGU (90)<br>GGC (3)<br>GGA (0)<br>GGG (0) | CAA (20)<br>CAG (0) | CCA (32)<br>CCU (3)<br>CCC (1)<br>CCG (0) | AUG (20) | UAC (33)<br>UAU (0) |

Consensus
oligonucleotides:     5'-GG$^T_C$CAACC$^A_T$ATGTAC

Synthesized
oligonucleotide      I.   5'-GTACATTGGTTG$^A_G$CC
pools complemen-
tary to above:       II.  5'-GTACATAGGTTG$^A_G$CC

FIGURE 1

```
CGACAGTAAATTTTGCCGAATTTAATAGCTTCTACTGAAAAACAGTGGACCATGTGAAAAGATGCATCTCATTTATCAA
         -280              -260              -240              -220

ACACATAATATTCAAGTGAGCCTTACTTCAATTGTATTGAAGTGCAAGAAAACCAAAAAGCAACAACAGGTTTTGGATA
         -200              -180              -160              -140

AGTACATATATAAGAGGGCCTTTTGTTCCCATCAAAAATGTTACTGTTCTTACGATTCATTTACGATTCAAGAATAGTT
         -120              -100               -80               -60
                                                                1
                                                                Met Arg Phe Pro Ser Ile
CAAACAAGAAGATTACAAACTATCAATTTCATACACAATATAAACGATTAAAAGA        ATG AGA TTT CCT TCA ATT
              -40               -20                            1
```

```
                                               20
Phe Thr Ala Val Leu Phe Ala Ala Ser Ser Ala Leu Ala Ala Pro Val Asn Thr Thr Thr
TTT ACT GCA GTT TTA TTC GCA GCA TCC TCC GCA TTA GCT GCT CCA GTC AAC ACT ACA ACA
 20                      40                       60

40
Glu Asp Glu Thr Ala Gln Ile Pro Ala Glu Ala Val Ile Gly Tyr Leu Asp Leu Glu Gly
GAA GAT GAA ACG GCA CAA ATT CCG GCT GAA GCT GTC ATC GGT TAC TTA GAT TTA GAA GGG
 80                     100                      120

60
Asp Phe Asp Val Ala Val Leu Pro Phe Ser Asn Ser Thr Asn Asn Gly Leu Leu Phe Ile
GAT TTC GAT GTT GCT GTT TTG CCA TTT TCC AAC AGC ACA AAT AAC GGG TTA TTG TTT ATA
140                     160                      180

80
Asn Thr Thr Ile Ala Ser Ile Ala Ala Lys Glu Glu Gly Val Ser Leu Asp Lys Arg Glu
AAT ACT ACT ATT GCC AGC ATT GCT GCT AAA GAA GAA GGG GTA TCT TTG GAT AAA AGA GAG
200                     220                      240

100
Ala Glu Ala | Trp His Trp Leu Gln Leu Lys Pro Gly Gln Pro Met Tyr | Lys Arg Glu Ala
GCT GAA GCT | TGG CAT TGG TTG CAA CTA AAA CCT GGC CAA CCA ATG TAC | AAG AGA GAA GCC
             *     * *     *   *
260                     280                      300

120
Glu Ala Glu Ala | Trp His Trp Leu Gln Leu Lys Pro Gly Gln Pro Met Tyr | Lys Arg Glu
GAA GCT GAA GCT | TGG CAT TGG CTG CAA CTA AAG CCT GGC CAA CCA ATG TAC | AAA AGA GAA
                 *     * *     *   *
320                     340                      360

140
Ala Asp Ala Glu Ala | Trp His Trp Leu Gln Leu Lys Pro Gly Gln Pro Met Tyr | Lys Arg
GCC GAC GCT GAA GCT | TGG CAT TGG CTG CAA CTA AAG CCT GGC CAA CCA ATG TAC | AAA AGA
                     *     * *     *   *
380                     400                      420

160             165
Glu Ala Asp Ala Glu Ala | Trp His Trp Leu Gln Leu Lys Pro Gly Gln Pro Met Tyr | End
GAA GCC GAC GCT GAA GCT | TGG CAT TGG TTG CAG TTA AAA CCC GGC CAA CCA ATG TAC | TAA
                         *     * *     *   *
440                     460                      480
```

```
GCCCGACTGATAACAACAGTGTAGATGTAACAAAGTCGACTTTGTTCCCACTGTACTTTTAGCTCGTACAAAATACAAT
        500              520              540              560

ATACTTTTCATTTCTCCGTAAACAACATGTTTTCCCATGTAATATCCTTTTCTATTTTTCGTTCCGTTACCAACTTTAC
        580              600              620              640

ACATACTTTATATAGCTATTCACTTCTATACACTAAAAAACTAAGACAATTTTAATTTTGCTGCCTGCCATATTTCAAT
        660              680              700              720

TTGTTATAAATTCCTATAATTTATCCTATTAGTAGCTAAAAAAAGATGAATGTGAATCGAATCCTAAGAGAATTC
        740              760              780              800
```

FIGURE 3

```
TTCTTCATTGGTACATCAATGCCAGCAACGATGTGCGCATCTGGGCGACGCCTGTAGTGATTGTTTTCAAGGTATCGAG
        -300                -280                -260                -240

CCAAACTATTCATCGTTACTGTTTCAAATATTCAGTTGTTTCAGTACAGAGTCGCCGTGGACCTAGTGAAACTTGGTGT
        -220                -200                -180                -160

CTTTACAGCGCAGAGACGAGGGCTTATATGTATAAAAGCTGTCCTTGATTCTGGTGTAGTTTGAGGTGTCCTTCCTATA
        -140                -120                -100                 -80

TCTGTTTTTATATTCTATATAATGGATAATTACTACCATCACCTGCATCAAATTCCAGTAAATTCACATATTGGAGAAA
         -60                 -40                 -20
```

```
 1                                          10                                          20
Met Lys Phe Ile Ser Thr Phe Leu Thr Phe Ile Leu Ala Ala Val Ser Val Thr Ala Ser
ATG AAA TTC ATT TCT ACC TTT CTC ACT TTT ATT TTA GCG GCC GTT TCT GTC ACT GCT AGT
 1                   20                              40                              60

30                                          40
Ser Asp Glu Asp Ile Ala Gln Val Pro Ala Glu Ala Ile Ile Gly Tyr Leu Asp Phe Gly
TCC GAT GAA GAT ATC GCT CAG GTG CCA GCC GAG GCC ATT ATT GGA TAC TTG GAT TTC GGA
                     80                             100                             120

50                                          60
Gly Asp His Asp Ile Ala Phe Leu Pro Phe Ser Asn Ala Thr Ala Ser Gly Leu Leu Phe
GGT GAT CAT GAC ATA GCT TTT TTA CCA TTC AGT AAC GCT ACC GCC AGT GGG CTA TTG TTT
                    140                             160                             180

70                                          80
Ile Asn Thr Thr Ile Ala Glu Ala Ala Glu Lys Glu Gln Asn Thr Thr Leu Ala Lys Arg
ATC AAC ACC ACT ATT GCT GAG GCG GCT GAA AAA GAG CAA AAC ACC ACT TTG GCG AAA AGA
                    200                             220                             240

90                                         100
Glu Ala Val Ala Asp Ala Trp His Trp Leu Asn Leu Arg Pro Gly Gln Pro Met Tyr Lys
GAG GCT GTT GCC GAC GCT TGG CAC TGG TTA AAT TTG AGA CCA GGC CAA CCA ATG TAC AAG
                                        *        * *
                    260                             280                             300

110                                         120
Arg Glu Ala Asn Ala Asp Ala Trp His Trp Leu Gln Leu Lys Pro Gly Gln Pro Met Tyr
AGA GAG GCC AAC GCT GAT GCT TGG CAC TGG TTG TAA CTC AAG CCA GGC CAA CCA ATG TAC
                                             *        * *
                    320                             340                             360
```

```
End
TGA AAAATGACCCTAAACTACTTCTAAACCCTCTCGATTTCTTTCACGTTCATACAACACCTAGTTTTATTTATTTTC
             380                 400                 420

TTTTCAATCTGAGTAGTTGAGTTTTCGATCACTCACATAGAACTATTTTTTGCCATTTAAATAAAGTATTCTCTCAAAT
    440                 460                 480                 500

GATGCGATACTATAATACTCTTTGCCATATATTACATTCATTCATAAATAGGCTATGTTTCTATATCCGTTTCCGATTC
    520                 540                 560                 580

TGTCTGCAAGCAAGGTTCCCTATCATTACCGGATTGTTCACTATGGTTGGAGCTC
    600                 620                 640
```

FIGURE 4

```
              1                   10                  20
MFα1       MetArgPheProSerIlePheThrAlaValLeuPheAlaAlaSerSerAlaLeuAlaAla
MFα2       MetLysPheIleSerThrPheLeuThrPhe---------------IleLeuAlaAla
Consensus  Met---Phe---Ser---Phe-------------------------LeuAlaAla 30                  40
MFα1       ProValAsnThr---ThrThrGluAspGluThrAlaGlnIleProAlaGluAlaValIle
MFα2       ValSerValThrAlaSerSerAspGluAspIleAlaGlnValProAlaGluAlaIleIle
Consensus  ------------Thr--------------------AlaGln---ProAlaGluAla---Ile 50                  60
MFα1       GlyTyrLeuAspLeuGluGlyAspPheAspValAlaValLeuProPheSerAsnSerThr
MFα2       GlyTyrLeuAspPheGlyGlyAspHisAspIleAlaPheLeuProPheSerAsnAlaThr
Consensus  GlyTyrLeuAsp------GlyAsp---Asp---Ala---LeuProPheSerAsn---Thr 70                  80
MFα1       AsnAsnGlyLeuLeuPheIleAsnThrThrIleAlaSerIleAlaAlaLysGluGluGly
MFα2       AlaSerGlyLeuLeuPheIleAsnThrThrIleAlaGluAlaAlaGluLysGluGlnAsn
Consensus  ------GlyLeuLeuPheIleAsnThrThrIleAla------Ala---LysGlu------

90                  100
MFα1       ValSerLeuAspLysArgGluAlaGlu------AlaTrpHisTrpLeuGlnLeuLysPro
MFα2       ThrThrLeuAlaLysArgGluAlaValAlaAspAlaTrpHisTrpLeuAsnLeuArgPro
Consensus  ------Leu---LysArgGluAla---------AlaTrpHisTrpLeu---Leu---Pro 110                 120
MFα1       GlyGlnProMetTyrLysArgGluAlaGluAlaGluAlaTrpHisTrpLeuGlnLeuLys
MFα2       GlyGlnProMetTyrLysArgGluAlaAsnAlaAspAlaTrpHisTrpLeuGlnLeuLys
Consensus  GlyGlnProMetTyrLysArgGluAla---Ala---AlaTrpHisTrpLeuGlnLeuLys 130                 140
MFα1       ProGlyGlnProMetTyrLysArgGluAlaAspAlaGluAlaTrpHisTrpLeuGlnLeu
MFα2       ProGlyGlnProMetTyr
Consensus  ProGlyGlnProMetTyr------------------------------------------

150                 160
MFα1       LysProGlyGlnProMetTyrLysArgGluAlaAspAlaGluAlaTrpHisTrpLeuGln
Consensus  ------------------------------------------------------------

168
MFα1       LeuLysProGlyGlnProMetTyr
Consensus  ------------------------
```

FIGURE 12

USE OF ALPHA FACTOR SEQUENCES IN YEAST EXPRESSION SYSTEMS

CROSS REFERENCE TO RELATED APPLICATIONS

This is a continuation of application(s) Ser. No. 07/552,719 filed on 16 Jul. 1990 now abandoned which is a continuation of Ser. No. 06/506,098 filed 20 Jun. 1983, now abandoned, which is a continuation-in-part of Ser. No. 06/488,323 filed 25 Apr. 1983, now abandoned. This application is related to commonly assigned applications Serial No. 06/438,236 filed Nov. 1, 1982, now U.S. Pat. No. 4,775,622, and its parent, and Ser. No. 06/488,337, filed Apr. 25, 1983, now abandoned, the disclosures of which are hereby incorporated by reference.

FIELD OF THE INVENTION

This invention is directed generally to recombinant DNA technology utilizing yeast host systems and expression vehicles that produce, process and secrete heterologous protein as discrete product unaccompanied by interfering amounts of unwanted presequence or other artifact of expression.

Proteins that are secreted through the cell membrane of the parent cell are ordinarily produced in the cell as a "pre"-protein. In that form, the protein is fused to an additional polypeptide sequence which presumably assists its secretion and localization. This additional protein, referred to as a "signal" polypeptide, is believed to be clipped from the secreted "mature" protein during the secretion process. Although the signal peptides of pre-proteins shaft some similarities, their primary structures differ considerably. The signal peptides even for a given organism exhibit this variation. For example, the signal for human growth hormone is substantially different from the signal for human insulin. This suggests that each protein has evolved with a signal sequence which is particularly well suited for translocation of that particular protein through a cell membrane.

This invention is based upon the discovery that a substantially mature protein is produced and often secreted by yeast when the DNA coding for the heterologous protein is operably attached to the DNA sequence of the promoter and/or signal peptide encoding portions of the yeast α-factor gene. (It will be apparent from the disclosure herein that yeast harbors at least two alpha factor genes. The use of "the alpha factor gene" is intended to include all such functional genes.) Thus, in a primary aspect, this invention is directed to the means and methods of obtaining useful quantities of heterologous protein from the medium of a yeast culture containing viable cells harboring expression vehicles containing DNA encoding the desired protein, wherein the DNA coding for this heterologous protein is operably connected to a DNA sequence comprising the promoter and/or signal portion of the yeast α-factor gene. Of enormous advantage is the enablement, by this invention, of obtaining useful, discrete protein product in the cell culture medium by expression of heterologous DNA in an easily modified plasmid.

The alpha factor of yeast contains a "pre-pro" sequence which is ordinarily removed from the α-factor upon the completed act of secretion. Operationally, therefore, the pre-pro sequence functions as a signal sequence in the process of secretion into the medium as will be further explained below. It is clear from the results obtained herein that the peptide which comprises the thus-defined signal sequence of alpha factor fused to a heterologous protein is successfully processed by the yeast organism so as to result in the secretion of the mature heterlogous protein into the surrounding medium. Therefore, the advantages obtained by use of this "pre-pro" signal are realized whether or not the expression of the signal/heterologous protein gene sequence is under the control of the alpha factor promoter or under the control of other promoters which are functional in yeast. Similarly, the results obtained demonstrate that the alpha factor promoter is effective in expressing the heterologous gene, and that such expression could be obtained without the intermediate insertion of the signal sequence into the expression vehicle. Accordingly, this invention is directed to the use of alpha factor promoter qua promoter in yeast systems for the expression of heterologous peptides and to the use of the alpha factor signal qua signal as a means for effecting processing and secretion of heterologous proteins produced as a result of expression in yeast.

The publications and other materials referred to herein to illuminate the background of the invention, and in particular cases, to provide additional detail respecting its practice, are incorporated herein by reference, and for convenience, are numerically referenced and grouped in the appended bibliography.

BACKGROUND OF THE INVENTION

Yeast organisms naturally transport a small number of certain homologous proteins to, and sometimes through, the plasma membrane as an essential contribution to cell surface growth and cell metabolism. As the cell buds as an incident of reproduction preparatory to formation of a daughter cell, additional proteins are required for formation of cell wall and plasma membrane as well as for metabolism. Some of these proteins must find their way to the site of function; hence, a secretory pathway is believed to exist (1). Certain homologous proteins involved in the above processes are formed by translation by ribosomes attached to the endoplasmic reticulum. Homologous proteins are those normally produced by the yeast species and required for its viability. Once formed, they migrate by transfer to Golgi apparatus, thence within vesicles to plasma membranes where some associate, or to some extent, penetrate into the space between the plasma membrane and the cell wall. A small number of homologous proteins seems to be exported completely through the cell wall, such as α-factor and killer toxin (2,3).

Again, the bud region of the cell seems to be the site of attraction for the vesicles and by their fusion to the inner surface of the bud they contribute to the overall growth of the plasma membrane, and presumably, the cell wall (4,5,6). It is controversial still whether glycosylation of the protein may assist, or is implicated, in the so-called secretory process. Further, by definition "secreted" proteins are believed to have a signal prepeptide, postulated to be associated with the transport or incorporation process at the membrane surface. However, the precise mechanism involved in the overall secretory process is not fully understood.

It was contemplated that recombinant DNA technology could provide valuable assistance in answering the open questions about the secretory process in yeast organisms and, given its proven applicability in enabling such, and other, organisms to produce copious quantities of heterologous polypeptide products endogenously (See, e.g., 7 to 17), in achieving appropriate manipulation of the yeast host so as to direct the secretion of heterologous protein in discrete, mature form. This has, in fact, been achieved and is the subject of copending application Ser. No. 06/438,236, and its parent, supra. In that application is described the discovery that a heterologous protein, initially expressed as a pre-protein with its native signal or hybrid thereof, can be processed and secreted by yeast as a mature protein.

SUMMARY OF THE INVENTION

This invention is based on the discovery that yeast organisms can be caused to produce, process and secrete protein that is normally heterologous to the yeast organism and not required for its viability, such that the protein can be obtained from the medium supporting the viable and reproducing yeast cells and in discrete form substantially unaccompanied by unwanted peptide presequence or other artifact of expression. For this purpose, a DNA sequence encoding the desired, heterologous protein is linked to the DNA sequence encoding the non-native (to the protein) signal sequence of yeast α-factor. Suitable yeast cells are transformed with expression vehicles harboring such DNA encoding a heterologous protein operably connected to the such DNA coding for the α-factor signal (pre-pro) peptide and a promoter. Upon expression of the sequence encoding the heterologous protein together with that encoding α-factor signal peptide, the expression product is processed and the mature heterologous protein is exported into the medium of the cell culture, from which it can be removed with relative ease, without need to disrupt the viable yeast cells. It is thus recovered in otherwise substantially mature form for use, without the need to remove unwanted presequence or certain other artifacts of expression (e.g., the methionine attached to the otherwise first N-terminus amino acid which is an expressional consequence of the AUG translational start signal codon). Thus, the medium can be obtained in a form substantially free of viable or disrupted (i.e., lysed or otherwise broken) cells and, since it contains the desired product, is susceptible to more easily employed purification techniques. Such product, after purification, is fit for use as intended. For example, human leukocyte interferon product finds use as a human antiviral and/or antitumor agent (See, generally, 7 to 17).

In summary, the present invention comprises the use of yeast alpha factor signal sequences and/or promoter to produce a protein normally heterologous to a yeast organism and not required for its viability, in discrete form unaccompanied by any substantial peptide presequence or other artifact of expression, as a product of yeast expression, processing and secretion. Further, this invention provides yeast cultures capable of producing such protein and resultant yeast culture media containing such protein as product. More specifically, the invention is directed to a process for producing heterologous proteins in yeast, and the expression vehicles and organisms employed in this process, wherein the alpha factor promoter is used to effect the expression of the foreign gene. Further, the invention is directed to the use of the signal (pre-pro) sequence for alpha factor to effect the processing and secretion of an expressed foreign protein, to a recombinant expression vehicle effectively harboring the alpha factor DNA sequences and to the cells transformed with such vehicles.

By the term "heterologous protein" as used herein is meant protein that is not normally produced by or required for viability of a yeast organism. This term contemplates the functional insertion of DNA encoding such protein, via recombinant DNA technology, into an expression vehicle, in turn used to transform a yeast organism host. Functional insertion of DNA denotes the insertion of DNA encoding the heterologous protein into an expression vector under control of the α-factor promoter and/or connected to the DNA sequence coding for the α-factor signal to obtain a hybrid preprotein, i.e., one which comprises the α-factor signal peptide fused to the heterologous protein. Examples of such heterologous protein are hormones, e.g., human growth hormone, bovine growth hormone, etc.; lymphokines; enzymes; interferons, e.g., human fibroblast, human immune and human and hybrid leukocyte interferons, bovine interferons etc.; viral antigens or immunogens, e.g., foot and mouth disease antigens, influenza antigenic protein, hepatitis core and surface antigens, etc.; factors incidental to growth, e.g. human insulin-like growth factor (IGF-1 and IGF-2), epidermal growth factor (EGF) and nerve growth factor (NGF) and various other polypeptides, e.g., rennin, human serum albumin, human insulin, various glycoproteins, etc.

"Secretion" as used herein means exportation of product through the plasma membrane and at least into or through the cell wall of the yeast organism into the medium supporting the cell culture. In this connection, it will be understood that in some instances, "secreted" product associates in some manner with the cell wall, perhaps necessitating a different purification procedure or a modification of the structure and function of the yeast host.

"Processing" means the cellular cleavage of the α-factor signal peptide from the mature protein so as to produce the heterologous protein unaccompanied by any substantial portion of the signal sequence or by extraneous peptide in—so-called discrete—mature form. By "extraneous" peptide is included peptide artifacts of expression such as methionine. Processing admits of cleavage of the signal polypeptide at a locus inconsequentially removed from the precise point of signal peptide union with mature protein.

BRIEF DESCRIPTION OF THE DRAWINGS

FIG. 1 illustrates the structure of pools of synthetic oligonucleotides used as hybridization probes to isolate the gene for α-factor.

FIGS. 3 and 4 are the nucleotide sequences of α-factor genes.

FIG. 12 illustrates the degree of consensus between the MFα1 and MFα2 polypeptides of FIGS. 3 and 4.

DETAILED DESCRIPTION OF A PREFERRED EMBODIMENT

Figure 2:
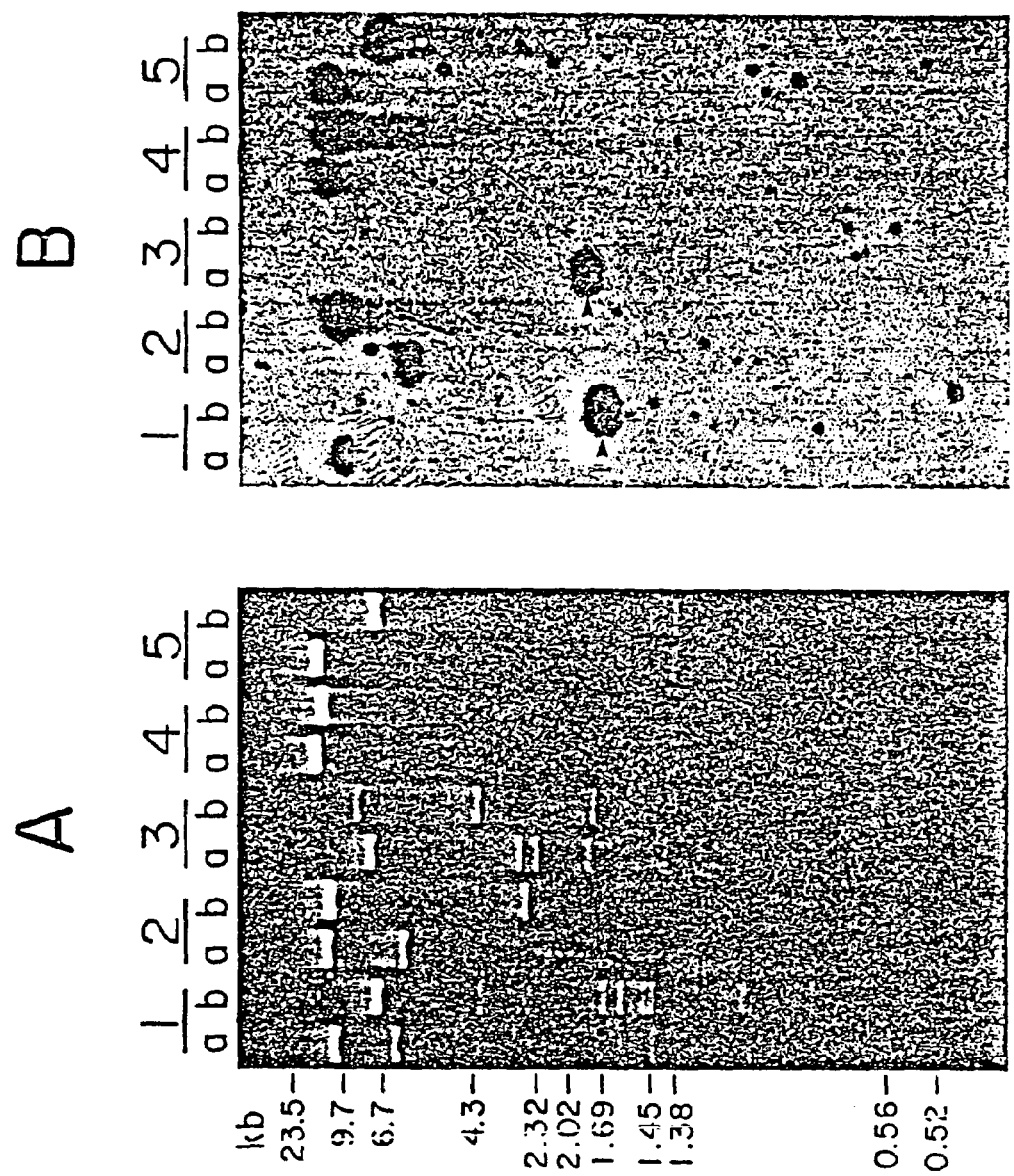
FIG. 2 illustrates the results of electrophoresis of DNA fragments obtained using the probes of FIG. 1.

The yeast *Saccharomyces cerevisiae* secretes only a limited number of proteins into the culture medium. One of the proteins that is found in the medium is α-pheromone or α-factor (2). Duntze and coworkers (18, 19) first determined that the α-factor is a family of four oligopeptides of 12–13 amino acid residues having the basic sequence $H_2N$-(Trp)-His-Trp-Leu-Gln-Leu-Lys-Pro-Gly-Gln-Pro-Met (or MetSO)-Tyr-COOH.

FIG. 3 shows the location of the four peptides in the unprocessed product of one of the α-factor genes, MFα-1. Only the "boxed" segments are secreted into the medium, the remaining sequences are not. It is not clear how much of the remaining sequence is "true" signal (pre) sequence, which is at least partially processed to effect secretion, and how much is "pro" sequence in the sense of a traditional precursor protein (e.g., prorennin, proinsulin.)

Similarly, only the "boxed" portions in product of the MFα2 gene shown in FIG. 4 are secreted, and the nature of the remaining sequences can be described analogously to that of those in MFα1.

During the reduction of this invention to practice, another group (44) succeeded in isolating and sequencing one of the genes for α-factor (MFα1) by methods different from those disclosed herein. As described below, two α-factor genes were isolated by us and expression vectors in which the DNA sequence for the promoter and signal peptide of α-factor was inserted in tandem with the DNA sequence coding for heterologous protein were constructed from one of them.

A. Bacterial and Yeast Strains

*E. coli* K-12 strain 294 (endA thi⁻hsr⁻hsm⁺)(ATTC 31446)(22) was used for bacterial transformations. Yeast strain 20B-12 (α, trp1 pep4) deposited without restriction in the American Type Culture Collection, ATCC No. 20626, on Mar. 5, 1982 was used as yeast host.

B. Growth Media

The routine yeast growth medium contained 1 percent Bacto-yeast extract, 2 percent Bacto-peptone and 2 percent dextrose. Yeast minimal medium contained 0.67 percent Bacto-yeast nitrogen base without amino acids, 2 percent dextrose and 3 percent gar. The minimal medium supplemented with 1M sorbitol was used for yeast transformations. Bacterial growth medium was LB (25) which was supplemented with 20 μg/ml ampicillin when used for transformation. S-agar plates used for colony screening contained per liter: 329 tryptone, 5 g NaCl, 15 g Difco agar and 0.29 NaOH to which ampicillin or chloramphenicol was added as indicated.

C. Transformations

*E. coli* 294 was transformed using a published procedure (23). Yeast were transformed essentially as described (21, 24).

D. Enzymes and DNA Preparations

Restriction enzymes were purchased from flew England Biolabs and Bethesda Research Laboratories and were used according to manufacturer's recommendations. T4 DNA ligase was from New England Biolabs and was used in 20 mM Tris-HCl (pH 7.5), 10 mM $MgCl_2$, 10 nM dithiothreitol, 1 mM ATP at 14° C. Calf alkaline phosphatase was purchased from Boehringer Mannheim and was used in 100 mM NaCl, 50 mM Tris-HCl (pH 7.4), 10 mM $MgSO_4$, 1 mM 2-mercapto-ethanol at 37° C.

Plasmid DNAs were prepared by the cleared lysate method (29) and were purified by Bio-Rad Agarose A-50 column chromatography. Small amounts of plasmid DNAs from individual *E. coli* transformants were prepared by a quick-screening procedure (20). DNA restriction fragments were isolated by electroelution from a 1 percent agarose gel followed by phenol/chloroform extraction and ethanol precipitation. Oligo-deoxynucleotide probes were prepared by the phosphotriester method (41).

E. Design of the Hybridization Probe

The 15-mer oligonucleotide probes for the α-factor gene were designed on the basis of the amino acid sequence of the pheromone (19) and yeast codon usage frequencies. The rationale is outlined in FIG. 1 where the last 5 amino acids of the α-factor and all the possible codons and their usage frequencies are given. (The codon usage is the total of 2 different glyceraldehyde-3-phosphate dehydrogenase clones (30, 31) and of alcohol dehydrogenase I.) The codon usage for these and other genes has recently been summarized (45). As can be seen from FIG. 1, virtually all possible sequences coding for the 5 amino acids are Included in the oligonucleotide sequence

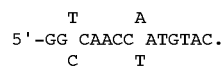

Accordingly, two pools consisting of two oligonucleotides each, and complementary to the above sequence, were synthesized. No other contiguous 5 amino acids in the pheromone could be covered with such a limited set of oligonucleotides.

F. Screening of Recombinant Plasmids

A genomic library, made by insertion of partially Sau3A-digested yeast DNA into the BamHI site of YRp7 (32), was screened for presence of α-factor gene clones. *E. coli* transformants were grown on nitrocellulose filter paper (Schleicher and Schuell, BA85) placed on S-agar plates containing 5 g/ml ampicillin. After 6 hours at 37° C., filters were transferred to S-agar plates containing 150 g/ml chloramphenicol. After 15 hours of amplification colonies were tested for hybridization using a modified in situ colony screening procedure (38). $^{32}$P-labeled (40) synthetic oligonucleotides described above were used as hybridization probes. Filters were hybridized overnight at 42° C. in 10 mM Tris (pH 7.5), 6 mM EDTA, 0.1 mM ATP, 1 mM sodium pyrophosphate, 0.8M NaCl, 1× Denhardt's solution, 0.5 percent NP-40, and 0.1 mg/ml *E. coli* TRNA. Filters were washed 3 times for 20 min. in 6×SSC at 30°. Dried filters were exposed to Kodak XR-2 X-ray film with Dupont Lightning-Plus intensifying screen at −80°.

G. Identification of Recombinant Plasmids Containing the α-Factor Gene

Approximately 4500 bacterial colonies containing recombinant plasmids were tested for in situ hybridization (38) with $^{32}$P-end-labeled oligonucleotide pool I (FIG. 1). Twenty-four plasmids hybridized to varying degrees. Small amounts of plasmid DNAs were prepared from these 24 colonies by the method of Birnboim and Doly (20) and tested for hybridization with the same probes after spotting the DNA samples on a nitrocellulose filter. Two of the 24 plasmids, designated as p51 and p52 respectively, hybridized strongly and were chosen for further study. The p51 and p52 plasmids also hybridized with the oligonucleotide pool II.

H. Subcloning of the Hybridizing Sequences

To characterize the inserts that hybridized with the synthetic probes, plasmid DNA prepared from the p51 and p52 clones was subjected to restriction enzyme analysis with EcoRI, SalI, HindIII, BamHI, and PstI. As seen in FIG. 2A, the 2 recombinant plasmids are quite dissimilar. Only EcoRI an PstI digestions of the two plasmids yielded one common fragment each. In both cases the common fragment is the TRP1 insert and the 1.38 PstI piece is the DNA between PstI sites in the TRP1 and the $amp^R$ genes.

The fragments that contained sequences complementary to the probe were identified by the method of Southern (42). FIG. 2B shows that, except in one case, digestion with all 5 restriction enzymes yielded a fragment that specifically hybridized with the probe. No hybridization was seen with any of the fragments produced by restriction of p52 DNA with HindIII.

The smallest restriction fragments that contained sequences complementary to the synthetic probes were the 1.7 kbp EcoRI fragment from p52 and the 1.8 kbp HindIII fragment from p51. These two DNA fragments were isolated from a preparative agarose gel by electroelution and separately ligated to appropriately cleaved plasmid pBR322 (33) DNA. The ligation mixture was used to transform $E.$ $coli$ 294 and the plasmid DNA from the transformants was analyzed by a quick-screen procedure (20). Two transformants, designated p53 and p56, containing the 1.7 kbp EcoRI and 1.8 kbp HindIII fragment inserts, respectively, were analyzed as follows: Plasmid DNA was prepared from p53 an p56 and digested separately with BamHI, ClaI, PvuI, PstI, and SalI. The resulting. DNA fragments were separated on a 1 percent agarose gel, transferred to nitrocellulose filter paper (42) and tested for hybridization with $^{32}$P-labeled probes. The analysis of the restriction digests and corresponding hybridization patterns of the p53 DNA, the recombinant plasmid containing the 1.7 kbp yeast DNA as an EcoRI fragment, showed that the yeast DNA in this clone contained one SalI and two PstI sites and that the sequence complementary to the probes was included within a 0.5 kbp PstI-SalI fragment. The HindIII fragment of yeast DNA in the clone p56 lacked recognition sites for these enzymes, and the linearized plasmid, resulting from cleavage at single recognition sites for these enzymes in the pBR322 vector, hybridized with the probes. This plasmid was then digested with a number of additional restriction endonucleases and the digests were analyzed by the method of Southern as described above. It was found that the hybridizing sequences in this plasmid were contained on a 1.3 kbp HindIII-SacI fragment.

The property of growth inhibition of "a" cells by α-factor was used to test whether or not the pheromone gene contained in the cloned 1.7 kbp EcoRI and 1.8 kbp HindIII fragments are functional. If an active α-factor pheromone gene were present in a plasmid, it would be expected significantly more pheromone would be synthesized in cells containing the multi-copy plasmid than in cells containing only the chromosomal copy (or copies) of the gene. The enhanced level of the α-factor could then be detected by an increase in the area of nongrowth in a lawn of responsive "a" cells. The 1.7 kbp fragment, isolated from EcoRI-digested p53 DNA, and the 1.8 kbp fragment, isolated from HindIII-digested p56 DNA, were separately ligated to a pBR322-based vector plasmid which contained the yeast selectable marker TRP1 and the yeast origin of replication from the 2 μm yeast plasmid (43). Yeast strain 20B-12 was separately transformed with these plasmids and with a control plasmid that lacked DNA sequences coding for the α-factor. The transformants were then compared for pheromone production. The transformants containing MFα1 or MFα2 coding sequences on plasmids produced significantly more α-factor than the same strain transformed with the control plasmid. We concluded that the 1.7 kbp EcoRI (MFα1) and 1.8 kbp HindIII (MFα2) fragments contain active α-factor pheromone genes. The result with MFα1 is consistent with that described by Kurjan and Herskowitz (44), as this gene corresponds to the gene described by them.

I. DNA Sequence Determination

DNA sequence determination was as previously described (45). Briefly, DNA sequences were obtained by the chain termination method (47) using recombinant phages M13 mp8 and mp9 (39) as the source for single-stranded "template" DNA and a synthetic oligonucleotide for priming $E.$ $coli$ DNA polymerase I (large fragment, Boehringer Mannheim) in the presence of α-$^{32}$P dCTP (400 Ci/mmole, Amersham). Reactions were electrophoresed on 5 percent polyacrylamide/8M urea "thin" gels (47). Gels were dried onto 3 MM paper (Whatman) and exposed to X-ray film for 2 to 12 hr.

The nucleotide sequences of large parts of the 1.7 kbp EcoRI fragment and the 1.3 kbp HindIII-SacI fragment are shown in FIG. 3 and FIG. 4, respectively. The p53 sequence contains an open reading frame coding for a protein of 165 amino acid residues which carries 4 internal repeat units within its C-terminal half. Each unit begins with Lys-Arg and ends with the α-factor sequence. Within each, unit the pair of basic residues is separated from the α-factor by several Glu (or Asp)-Ala dipeptide repeats. The N-terminal half of the protein starts with a highly hydrophobic sequence of 22 amino acids which probably represents a signal sequence for secretion. The 61 amino acid residues between this hydrophobic sequence and the first repeat unit include 3 possible recognition sites for N-glycosylation (indicated by bars in FIG. 3). The organization of the pheromone gene contained in p53 clone is identical to the MFa gene recently described by Kurjan and Herskowitz (44). This gene differs from MFα1 at 4 positions. It contains T (instead of C) residues at positions −8 and −7, and 125 and an A (instead of C) residue at position 604. Because of the difference at position 125 there is a TTA (Leu) rather than TCA (Ser) codon at amino acid position 42. We have designated the gene contained in p53 as MFα1.

A different α-factor gene, MFα2, is present in the p56 clone. The organization of this gene (FIG. 4) is similar, but not identical, to the MFα1. The α-factor encoded by this gene is apparently made as a precursor protein of 120 amino acid residues containing two copies of the pheromone. One of the α-pheromone tridecapeptides contained in the putative precursor is identical to the pheromone copies encoded by the MFα1 gene, whereas the second copy contains a Gln→Asn and a Lys→Arg.

The organization of these precursors is strikingly similar to that of certain mammalian precursors for neuroendocrine peptides. Thus, like the propiomelanocortin (48, 49), proenkephalin (50–52), and prodynorphin (53), the yeast precursors contain multiple peptide units destined for secretion. In all these precursors the secreted unit is contained on the C-terminal half of the precursor. The N-terminal half of the molecules carry possible glycosylation sites. As is the case for the mammalian multifunctional precursors, glycosylation may be involved in the correct processing of the α-factor precursor. However, the actual processing steps for the yeast precursor seem to be unpredictably different from those of mammalian precursor proteins. Whereas the pairs of basic residues (Lys-Arg) providing sites for release directly flank the secreted peptide in the mammalian precursors, cleavage at these sites in the α-factor precursor would release the pheromone units with several additional amino acids at the N-terminus (see FIGS. 3 and 4). These N-terminus extensions would consist of repeating —X-Ala- sequences in the precursors encoded by both MFα1 and MFα2 genes. Recent experiments (54, 55) indicate that the last step in the processing of the α-factor precursors is the removal of these sequences by dipeptidyl amino peptidases. The bee venom melittin (56) and the frog skin caerulein (57) precursors are apparently processed by similar mechanisms.

J. Construction of a Plasmid for Expression and Secretion of Human Interferon

Although, as discussed above, our DNA sequence data suggest that the α-factor is synthesized as precursor proteins of 165 and 120 amino acids, no such proteins have been described. The processing and secretion mechanism of α-factor is not known. Recent studies, however, with altered α-factor indicate that the last step in the production of mature α-factor is apparently the removal of the glu-ala or asp-ala units before the release of the α-factor oligopeptides of 12–13 amino acids having the basic sequence H$_2$N-(Trp)-His-Trp-Leu-Gln-Leu-Pro-Gly-Gln-Pro-Met (or MetSO)-Tyr-COOH.

Figure 5:
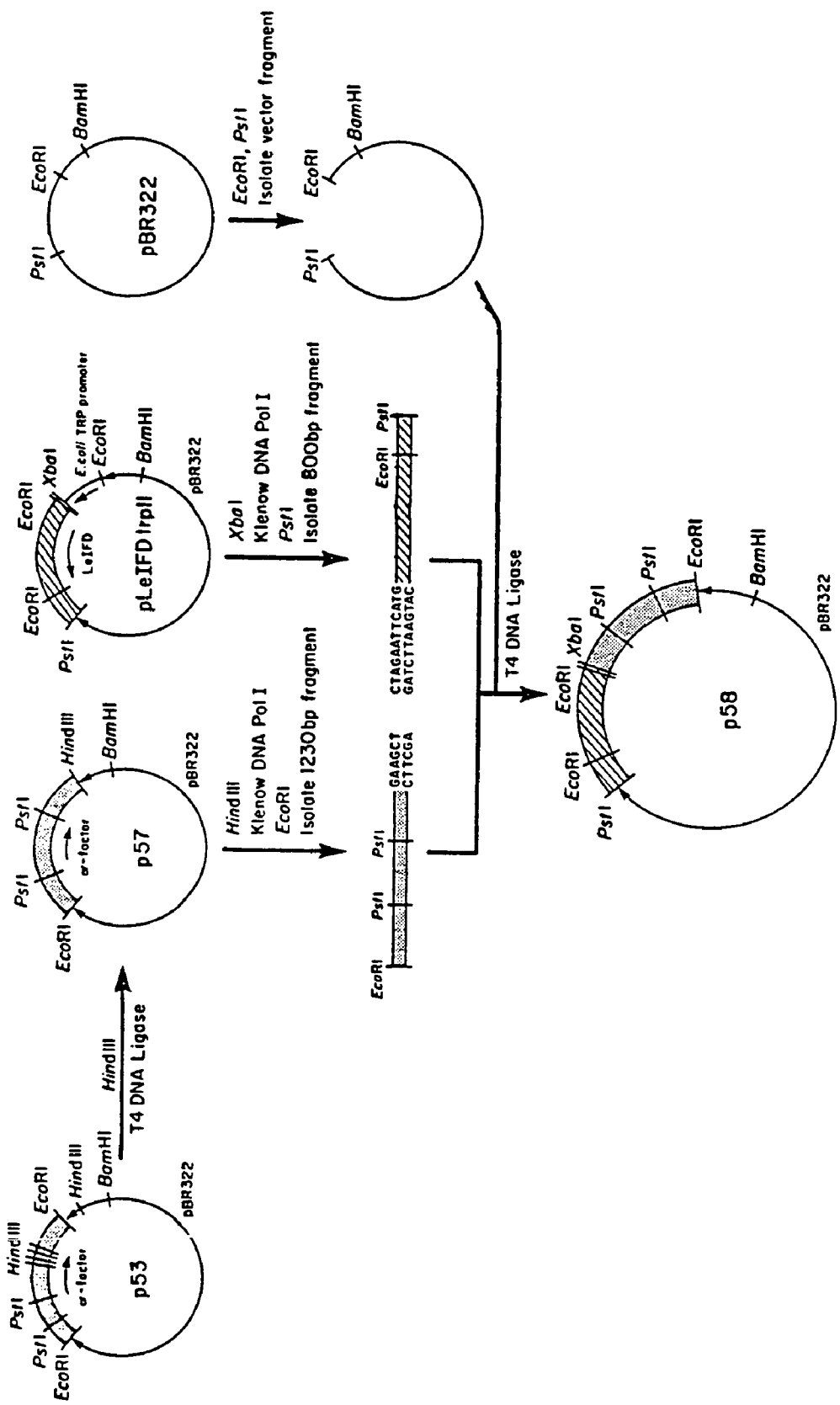
FIG. 5 illustrates the scheme for joining the gene for human interferon D with the gene for the α-factor promoter and signal sequence.
Figure 6:
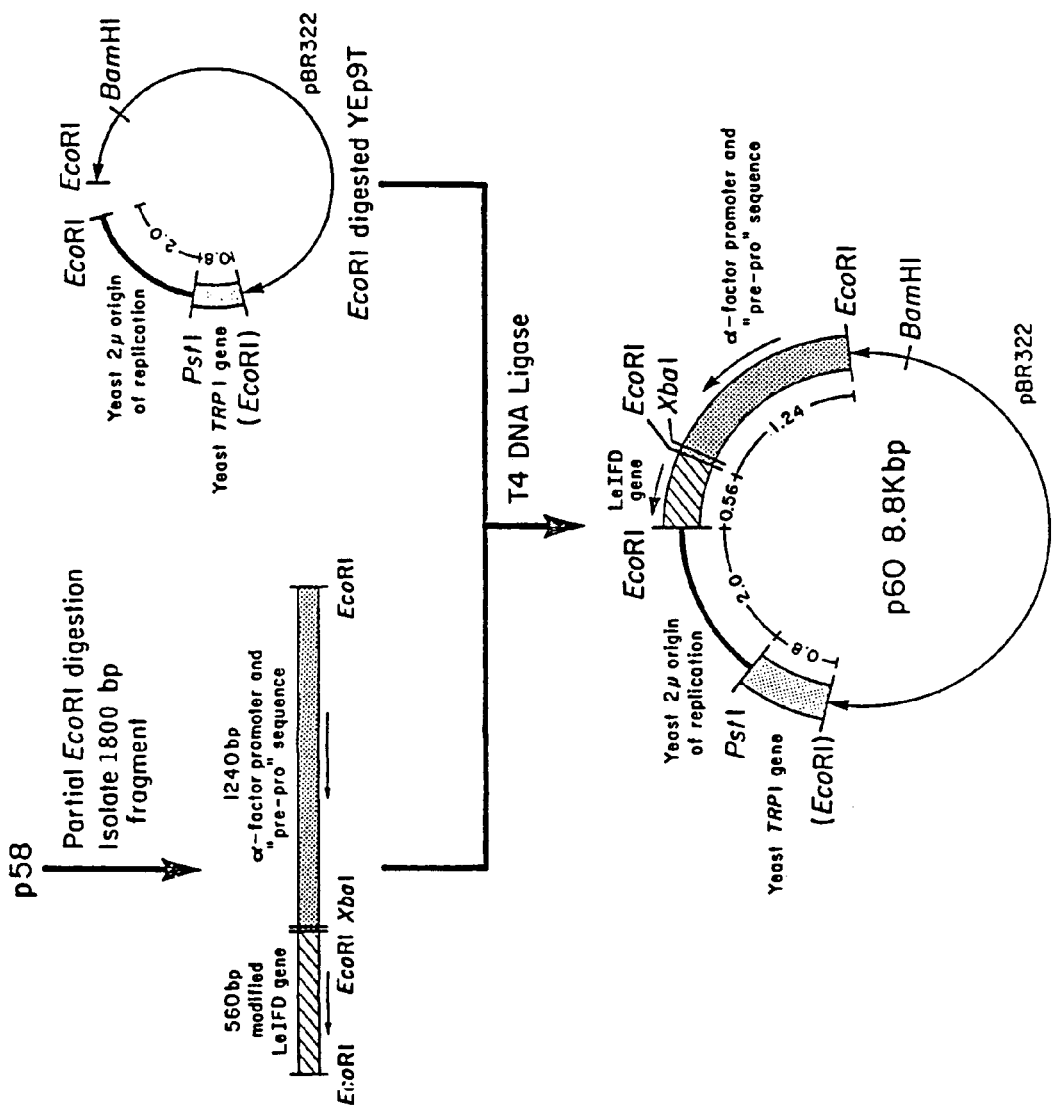
FIG. 6 illustrates the scheme for construction of a yeast expression plasmid for expression of human interferon D (IFN-$\alpha_1$).
Figure 7:
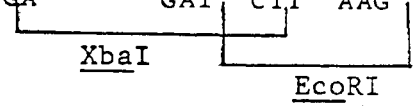
FIG. 7 depicts the protein and DNA sequence at the junction of the α-factor signal sequence and the modified IFN-$\alpha_1$ gene.

The preparation of a plasmid to demonstrate the usefulness of the α-factor promoter and the α-factor presequences for expression and secretion of heterologous gene products is outlined in FIG. 5. The DNA sequences coding for the α-factor presequences for expression and secretion of heterologous gene products is outlined in FIG. 5. The DNA sequences coding for the α-factor peptides were removed from one of the α-factor clones (p53) such that the resulting plasmid, p57, contained the promoter sequences and the sequence corresponding to 89 amino acids of the α-factor "prepro" protein. This sequence was then joined with human interferon D (IFN-α$_1$) gene to form plasmid p58. The human interferon D gene (58) was modified such that DNA sequences corresponding to Leu-Glu-Phe had been added before the initiating methionine codon. After modified interferon D gene had been joined with the α-factor "prepro" and the promoter sequences, these sequences were isolated and inserted into a yeast-E. coli shuttle plasmid YEp9T (FIG. 6). The plasmid YEp9T had been previously made by replacing the EcoRI-SalI fragment in plasmid YEp1PT (59) with the EcoRI-SalI fragment from pBR322. This plasmid contains the pBR322 (33) DNA needed for its selection and replication in E. coli. In addition, it contains the yeast TRP1 gene on an EcoRI to PstI fragment from chromosome IV (34–36) and a yeast origin of replication on a PstI to EcoRI fragment from the endogenous 2μ plasmid DNA. These two DNA fragments from yeast allow for its selection in yeast and for its autonomous replication and maintenance as a plasmid. The resulting plasmid, p60, with the indicated orientation of the insert was selected because the 2μ origin contains a transcription termination/polyadenylation signal (37). The DNA sequence at the junction of the α-factor "prepro" sequence and the modified LeIFN-D gene present in p60 is shown in FIG. 7. The p60 plasmid was introduced into the yeast strain 20B-12 and the trp$^+$ transformants were grown and assayed for interferon production.

K. Interferon Assay of Growth Medium and Cell Extracts

Individual colonies of the transformants were grown at 30° C. in 20 ml YNB+CAA to an A$_{660}$ of approximately 10. For assay 10 ml aliquot was centrifuged at 7 K rpm for 10 minutes in a Sorval SM24 rotor. Various dilutions of supernate (media) were assayed. The cells were resuspended in 0.5 ml 7M guanidine-HCl containing an equal volume of glass beads and vortexed for 2 minutes at high speed. Both the cell lysate and the medium were then diluted into PBS/BSA (150 mM NaCl, 20 mM sodium phosphate (pH=7.9), and 0.5 percent bovine serum albumin) for bioassay. Extracts of yeast were assayed for interferon by comparison with interferon standards by the cytopathic effect (CPE) inhibition assay (26). Up to one hundred million units of interferon per liter of growth medium was found. The cell extracts also yielded interferon at the rate of 100×10$^6$ units per liter of culture.

L. Purification of Interferon from the Medium

Figure 8:
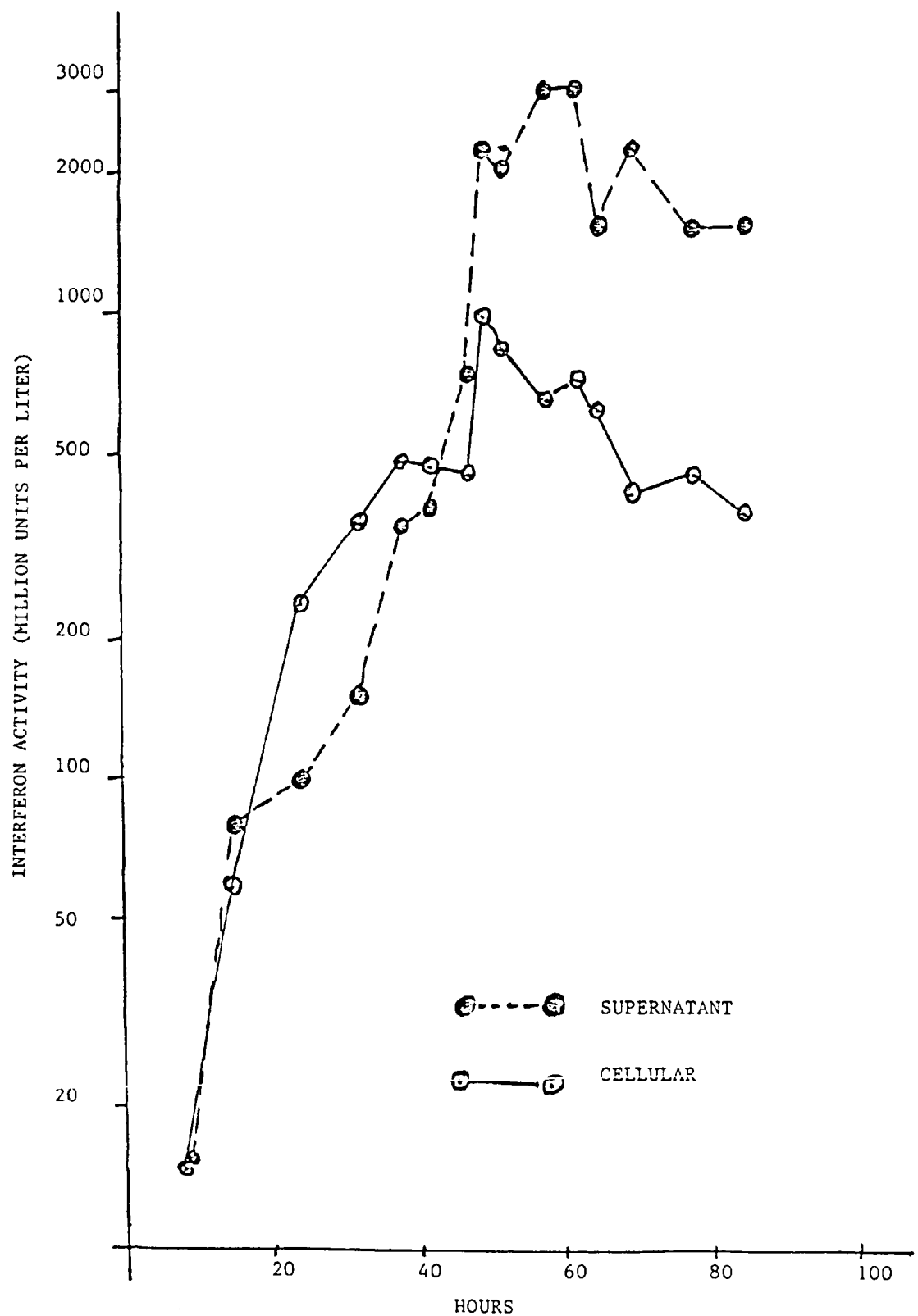
FIG. 8 shows the levels of IFN-$\alpha_1$ in the medium and cell extracts of a culture of a yeast transformant expressing IFN-$\alpha_1$.

A single colony of yeast strain p60/20B-12 was grown at 30° C. in 500 ml YNB+CAA to an A$_{660}$ of 2.4. Five hundred ml of this culture was diluted to 5 L with YNB+CAA to give an A$_{660}$ of 0.21; the resultant 5 L culture was grown at 30° C. until A$_{660}$=70. At this time the 5 L culture was harvested by centrifugation at 7,000 rpm for 10 minutes. Ten ml aliquots were withdrawn periodically during the fermentation to measure optical density, interferon production and secretion. Before assay, each aliquot was centrifuged for 5 minutes in a bench-top refrigerated centrifuge to separate the cells from the medium. The medium and cells were assayed as described above (see FIG. 8). Two different fermentations were done. The peak activity of interferon in the media were 3×10$^9$ and 2×10$^9$ units per liter, respectively. The interferon activity in the cell extracts were 1×10$^9$ and 2×10$^9$ units per liter of culture.

One and a half liters of frozen medium were concentrated and dialyzed against 25 mM Tris, 10 mM EDTA, pH 8.0 in a 2.5 liter Amicon stirred cell (Amicon 2000) using a YM-5 ultrafiltration membrane to a final volume of 116 ml. A sample of the retentate was sequenced directly. Another sample of the retentate was acetone precipitated and sequenced.

One ml of the concentrated medium was precipitated with 4 ml acetone, spun in a microfuge and washed with acetone. The pellet was resuspended in 0.1 percent TFA and further purified by HPLC on a Synchropak RP-P column. The column was eluted with a linear gradient of 0 to 100 percent acetonitrile in 0.1 percent TFA in 60 minutes. A 12 μg sample of purified IFN-αAD was chromatographed as a control. The peaks of absorbance at 280 nm were sequenced.

M. N-terminal Amino Acid Sequence of Interferon from Growth Medium

Sequence analysis was based on the Edman degradation (27). Liquid samples were introduced into the cap of a modified Beckman 890B spinning cap sequencer. Polybrene™ was used as a carrier in the cap (28). Reagents used were Beckman's sequence grade 0.1 molar Quadrol buffer, phenyl-isothiocynate, and heptafluorabutyric acid. Norleucine was added during each cycle with the Quadrol buffer to serve as an internal standard. The presence of PTH-norleucine in each chromatogram aided in the identification of PTH amino acids by retention time. The amino acid sequence analysis showed only one species of interferon molecule with the NH$_2$-terminal sequence NH$_2$-Glu-Ala- Glu-Ala-Leu-Glu-Phe-Met. The Met results from the start codon at the N terminus of the interferon gene, and thus the protein produced contains 7 extra amino acids, three from the construction, i.e., Leu-Glu-Phe (see FIG. 7) and 4 from the presequence of α-factor, i.e., Glu-Ala-Glu-Ala. The polypeptide containing this 7 amino acid N-terminal extension retains interferon activity.

N. Expression and Secretion of Other Heterologous Gene Products

Figure 9:
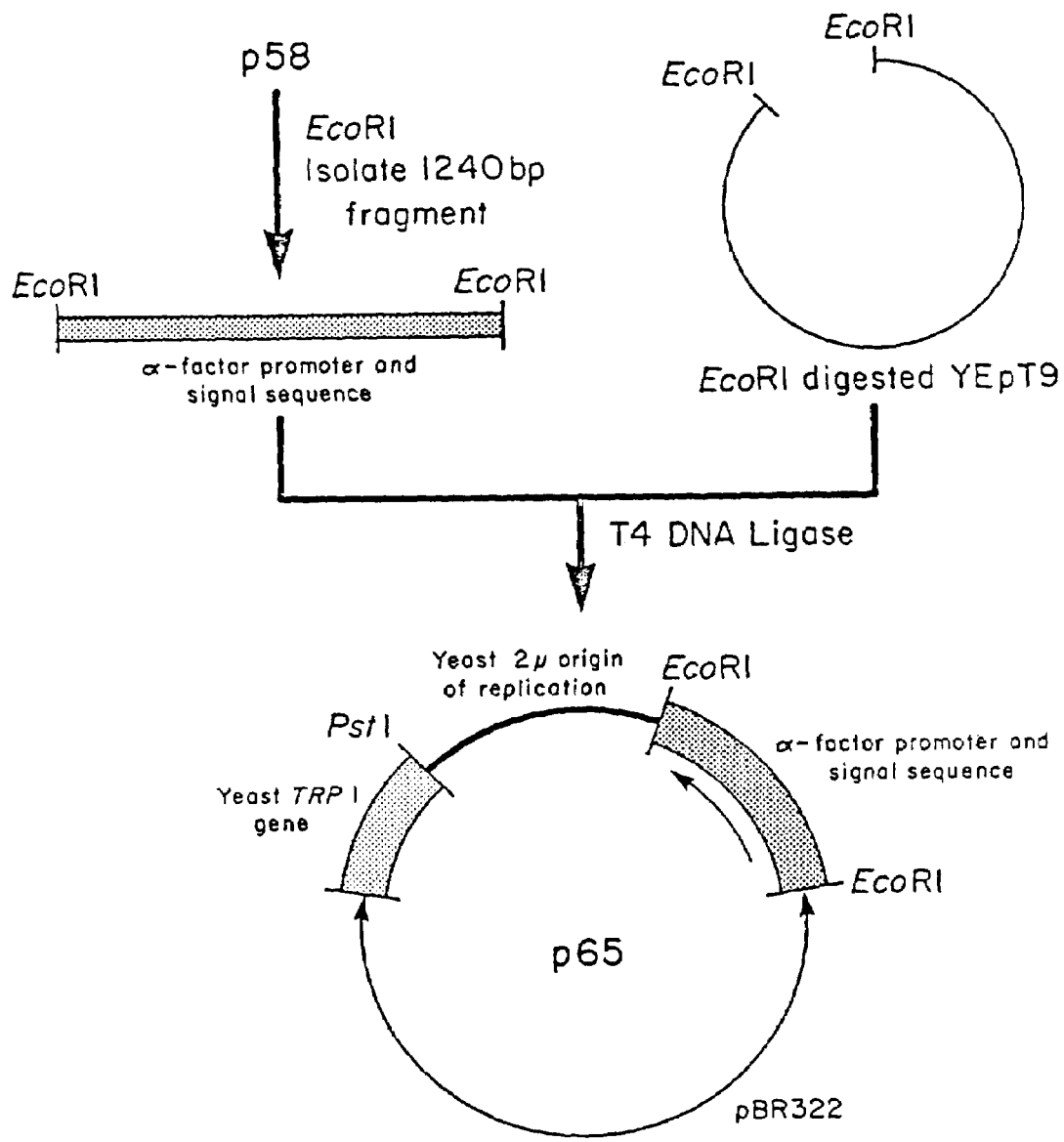
FIG. 9 illustrates the scheme for construction of a yeast/*E. coli* shuttle vector for expression of heterologous genes using the α-factor promoter and signal polypeptide gene sequences.

In the process of testing the utility of the α-factor promoter and "prepro"-sequence, restriction endonuclease sites were created at the end of the α-factor "prepro"-sequence (see FIG. 7) such that the promoter and the "prepro"-sequence could be isolated as a portable restriction fragment. An appropriate plasmid could then be constructed to test the efficacy of this expression and secretion system for any heterologous gene containing suitable "sticky" ends. For this purpose an expression plasmid p65, was constructed as shown in FIG. 9. This plasmid, like YEp9T, contains the origins of replication for *E. coli* and yeast as well as selective markers for selection in each; of these two organisms. It also contains a convenient EcoRI site for gene insertion so that any gene that is contained on an EcoRI fragment where the first codon of the gene is immediately preceded by the EcoRI site could be tested for the synthesis and secretion of the corresponding protein.

The plasmid p65 was partially digested with EcoRI the linear molecules isolated, and ligated with EcoRI fragments containing various genes. After transformation of *E. coli*, plasmids that contained the inserts in the appropriate orientation were selected. For expression the fragment must be inserted at the EcoRI site following the promoter with the 5'

297,380, filed Aug. 28, 1981, (HSA) (abandoned); and U.S. Pat. No. 06/312,489 filed Oct. 19, 1981 (yIFN) (abandoned in favor of Continuation S.N. 06/746,813, now U.S. Pat. No. 4,762,791) and elsewhere, e.g., in *Interferons* edited by Merigan, et al., Academic Press, Inc. (1982), Proceedings of the Symposium on "Chemistry and Biology of Interferons: Relationship to Therapeutics", held Mar. 8–12, 1982, Squaw Valley, Calif.; Lawn, et al. *Nucleic Acids Research* 9, 6103 (1981); Gray, et al., *Nature* 295, 503 (1982).

Figure 10:
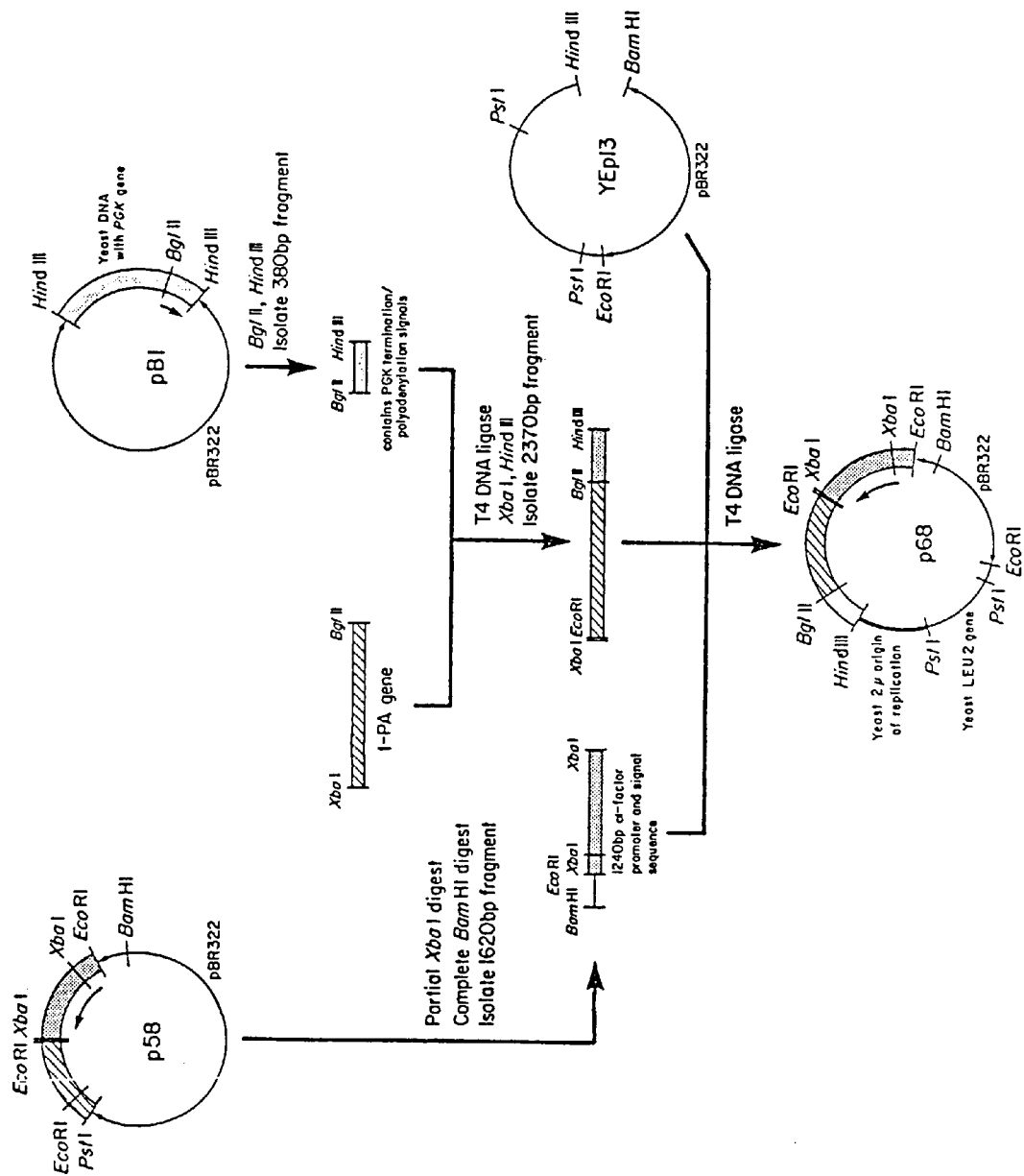
FIG. 10 illustrates the assembly of a yeast/*E. coli* plasmid for expression of tissue plasminogen activator.

Because of the placement of the restriction sites in the t-PA and rennin genes it was not practical to construct expression plasmids directly as above, but a modified approach was taken. The construction of the t-PA expression plasmid is illustrated in FIG. 10 using plasmid pt-PAtrp 12 (60) to obtain the t-PA gene by excision with XbaI and BglII, pB1 (described in Ser. No. 06/438,236, supra) and YEp13 (43). The rennin expression plasmid was assembled in analogous manner using the rennin gene obtained by XbaI-BclI excision of pRI (described in U.S. Pat. No. 452,227 filed Dec. 22, 1982, abandoned). These two plasmids contain the LEU2 gene for selection in yeast. Therefore an α leu2 yeast strain was used for transformation with these plasmids. The prorennin expression plasmid pR1 was constructed by incubating EcoR1-Pst I cleaved y-IMM plasmid with 5' and 3' segments in the Dresence of T4 ligase. y-IMM is a pBR 322 derived plasmid described in U.S. Appln. Ser. No. 312,489, filed Oct. 19, 1981 (abandoned in favor of Continuation of Ser. No. 746,813. now U.S. Pat. No. 4,762, 791) and Gray, et al., supra.

The 5' end fragment was a ligation of a synthetic fragment and a fragment derived from clone PFLA, as described below. The synthetic fragment has the structure:

```
                     [Met] [Ala] [Glu] [Ile] [Thr]
          d A A T T C A T G G C A G A A A T A A C A A G
                    G T A C C G T C T T T A T T G T T C C T A G d
                reading direction--->
``` end of the gene connected to that site. This orientation creates the junction between the α-factor signal sequence and the heterologous gene as previously shown for LeIF-D (see FIG. 7).

Table I lists genes that have been thus tested with the α-factor promoter and signal sequence.

TABLE I

Expression and Secretion of Other Heterologous Genes Using the α-Factor Promoter and Signal Sequence

| Gene | Growth Vessel | Products per Liter Cellular | Medium |
|---|---|---|---|
| Human Interferon γ | Shake-flask | $10^5$ units | trace |
| Human Serum Albumin | Fermentor | 25 mg | 3 mg |
| Bovine Interferon α1 | Fermentor | $100 \times 10^6$ U | $200 \times 10^6$ U |
| Bovine Interferon α2 | Fermentor | $400 \times 10^6$ U | $60 \times 10^6$ U |
| Tissue Plasminogen Activator | Shake-Flask | 20 μg | 20 μg |
| Rennin | Shake-Flask | 100 μpg | trace |
| Human Insulin-Like Growth Factor | Fermentor | 1–5 mg | 3 mg |

The expression of the first 4 genes was achieved by the insertion of EcoRI fragments into p65 as described above. The genes were obtained by EcoRI digestion of plasmids containing them as described in U.S. Pat. No. 06/438,128 filed Nov. 1, 1982 (BoIFN) (abandoned); U.S. Pat. No.

This sequence contains an EcoRI site at the "upstream end" an ATG start codon, followed by sequences coding for the first four amino acids in prorennin, and terminates in a BamH1 site.

The cloned fragment to which this synthetic fragment is ligated in order to form the 5' end of the gene comprises a Xma-BamHI fragment of approximately 440 base pairs derived from the 5' end of the gene.

The appropriate 440 bp fragment was obtained from cDNA derived from unfractionated mRNA, using as primer, dGATCCGTCGAATTCGG, i.e., the "primer probe". The cDNA formed using this primer was size fractionated as set forth above and fragments having more than 1,000 base pairs inserted into the PstI site of pBR322 for cloning. The resulting clones were selected using both Tth probe and the primer/probe as probes. Only colonies hybridizing with both were selected. From 1,280 transformed colonies, about 300 colonies were obtained which showed hybridization with both probes. These were examined for presence of the 5' portion of the prorennin sequence as follows:

The results of a series of double digestions using Ava I-Pvu I, AvaI-BamHI, BglIBamHI, and BglI-EcoRI were analyzed. Advantage was thus taken of the known Pvu I and Bgl I sites, each 125 base pairs either side of the pBR322 Pst site utilized for insertion of the cDNA sequence. These digestions provide suitable fragments for analysis.

The desired clone, PFLA, was selected by analysis of acrylamide gel electrophoresis performed on the above double digests of mini preps prepared from the identified clones. Plasmids were then isolated from PFLA clone, double digested with BamH I and XmaI, and the 440 bp fragment recovered by gel electrophoresis.

The "complete" 5' end was then created by a standard ligation reaction utilizing the synthetic fragment and the PFLA clone BamHI-XmaI fragment with T4 ligase followed by cleavage with XmaI and EcoRI. The resulting ligated sequences were purified on acrylamide gel electrophoresis selecting for the appropriate 455 base pair fragment.

The 3' and fragment was prepared in an manner analogous to that used to prepare the PFLA clone. cDNA containing >1000 bp formed from unfractionated messenger RNA using oligo-dT as primer, was cloned as above, and colonies selected with Tth probe. Approximately 50 colonies resulted. The desired clone was selected by analyzing the results of gel electrophoresis formed on plasmid minipreps which were double digested with BamHI/BglI, PvuI/BamHI, EcoR1/BglI, and PvuI/EcoR I again taking advantage of the PvuI and BglI sites flanking the PstI insert site. The plasmids from the desired colony were isolated then cleaved with Xma I and Pst I and electophoresed to isolate the 800 bp sequence of the "3–375" fragment. The "3–375" fragment extends from the Xma site congruent with that from the PFLA fragment, past the end of the gene to the Pst I insertion site.

The transformants carrying various expression plasmids were grown in appropriate media. The cultures were fractionated into supernatants and cells. The supernatants (media) and cell extracts were assayed for the expression and secretion of various gene products. The bovine interferon activity was assayed by comparison with interferon standards by cytopathic effects. The amounts of other products in the medium and cell extracts were determined by radioimmunoassays. The values listed in the table are the peak activities. We have determined that both cellular and secreted t-PA molecules possess biological activity.

O. Characterization of Secreted Bovine Interferon

The bovine interferon-$\alpha_1$ secreted into culture medium has been purified and characterized as described below.

7 liters of culture medium was adjusted to pH 8.02 with sodium hydroxide. This solution was then loaded onto a 2.5×18 cm Nugel ACA column pre-equilibrated with 50 mM tris, pH 8.0. After loading, the column was washed with 50 mM Tris, 1 percent (w/v) PEG 8000, pH 8.0 until $A_{280}$ was approximately zero. The column was then eluted with 100 mM ammonium acetate, 2 percent (w/v) PEG 8000, pH 5.0 followed by 20 mM glycine, 2.5 percent (w/v) PEG 8000, pH 2.0. The majority of the interferon activity eluted in a single peak during the pH 5.0 elution. The pooled material from the Nugel column (88 mL, 150 M units) was loaded onto a 2.5×5.0 cm SE-53 column pre-equilibrated with 25 mM ammonium acetate, pH 5.0. The interferon activity eluted in a single peak during the sodium chloride elution. This pool contained 14 mg protein, 106M units in 11 mL. The purity of this material as judged by SDS PAGE was approximately 80–90 percent.

Ten ml of the SE-53 pool was applied to a 2.5×18 cm Sephacryl S-300 column equilibrated in 25 mM sodium phosphate, pH 6.0. The column was eluted with this buffer and the interferon activity eluted in a single peak. This final pool contains 8 mg protein, 113 M units in 17 mL.

N-terminal sequence analysis of the protein present in the SE-53 pool indicates that the bovine interferon secreted by yeast has been processed at three distinct sites. The three sites of processing and the relative amounts of each are as follows:

```
        -8        -6           -3           +1
. . . lys-arg-glu-ala-glu-ala-leu-glu-phe-met-cys-
         63 pct. 13 pct.     24 pct.

his-leu-pro-his . . .
```

As shown above, met immediately precedes the N-terminus of the bovine interferon; the short peptide extensions do not result in loss of interferon activity.

Production and Secretion of Mature Heterologous Proteins

In both cases (human IFN-$\alpha_1$, and bovine IFN-$\alpha_1$) where the N-terminal amino acid sequence of the secreted polypeptides was determined, the proteins contained extensions of 2 to 7 amino acids in addition to the initiating methionine. Although these polypeptides have biological activity, it would be preferable to produce and secrete into the growth medium proteins that are identical to the proteins from the natural sources.

Figure 11:
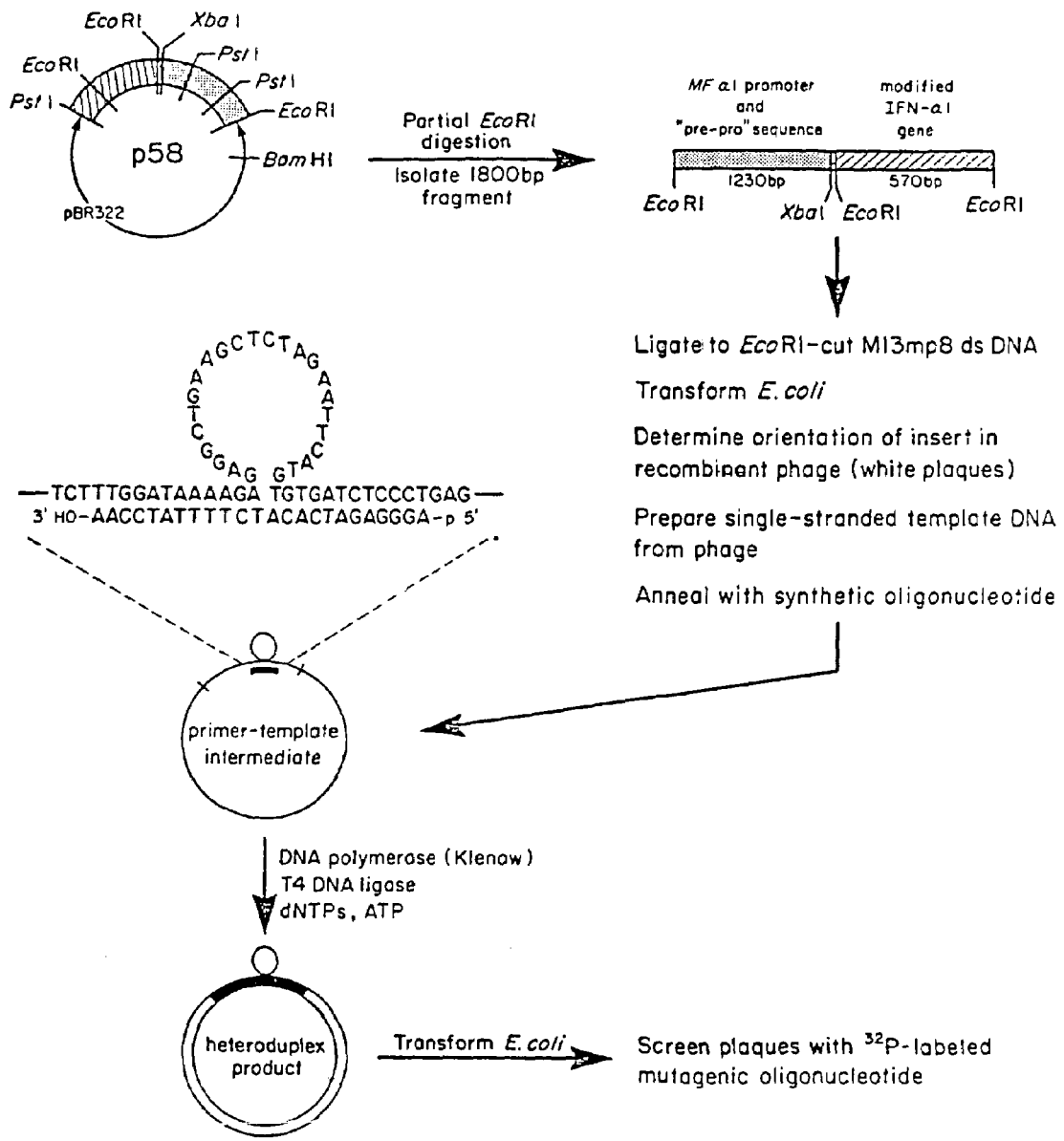
FIG. 11 depicts the construction used to effect the production of mature heterologous proteins (human interferon illustrated) as a product of expression with partial alpha factor signal sequence, processing of the alpha factor component and secretion of the mature protein into the supporting medium.

In order to produce the interferon molecule that contains cysteine as the N-terminal amino acid (as is the case with the natural IFN-$\alpha_1$) we needed to modify the junction between the factor "pre-pro" sequence and the IFN-$\alpha_1$ gene such that the removal of the modified "pre-pro" sequence will result in release of a mature interferon molecule containing the natural N-terminus. An outline of the procedure to obtain such a junction is shown in FIG. 11. A DNA fragment containing the MF$\alpha$1 promoter and "pre-pro" sequence and the modified IFN-$\alpha_1$ gene was isolated and cloned into the EcoRI site of M13 mp8 (61). Single-stranded DNA template was prepared from the recombinant phage containing the insert in the appropriate orientation. This template was annealed with a phosphorylated oligonucleotide. The synthetic oligonucleotide is 24 bases long and is complementary to 12 bases coding for leu-asp-lys-arg near the C-terminus of the "pre-pro" sequence and to 12 bases coding for cys-asp-leu-pro, the first 4 amino acids of natural IFN-$\alpha_1$. This primer-templated intermediate was subjected to extension and ligation reaction at 23° C. for 2 hours in the presence of 500 mMdATP, 100 mMdTTP, 100 mMdGTP, 100 mMdCTP, 20 mMdATP, 3 units DNA polymerase (Klenow), and 400 units t4 DNA ligase in 10 mM Tris pH7.4, 50 mM NaCl and 10 mM Mg 504. Then additional 3 units of DNA polymerase (Klenow) and 400 units of T4 DNA ligase was added and mixture incubated for 2 hours at 23° C. followed by incubation at 14° C. for 15 hours. This mixture was used to transform *E. coli* JM101 (62). The phage plaques were screened for hybridization with the $^{32}$P-labeled oligonucleotide. Templated DNA from 2 positive recombinant phages was prepared and sequenced using a primer complementary to IFn-$\alpha_1$, DNA. Double stranded DNA from one revcombinant phage that contained the desired deletion (deletion of 2.4 nucleotides shown as a loop in FIG. 11) was prepared. The EcoRI fragment containing the modified junction between the "pro—pro" sequence and the IFN-$\alpha_1$ gene was isolated and ligated to EcoRI cleaved YEP9T. After transformation of *E. coli* with the mixture a plasmid (p76) With correct orientation of the insert was chosen for further study.

p76 DNA was prepared from *E. coli* and used to transform 20B-12 strain (ATCC 20626) of yeast. Ten liter culture of one transformant was grown and the culture medium was centrifuged to separate the medium from the cells.

500 ml of yeast medium was dialyzed into 25 nM Tris, pH8.0, 10 mM EDTA. The dialyzed media was then run through an immuno affinity column containing monoclonal antibody to natural monoclonal antibody to natural LeIFa. After washing with 24 mM TRIS pH8.0, 10 mM EDTA, the interferon activity was eluted with 0.2M acetic acid. The majority of interferon activity was found in Fraction No. 45. 200 µl of this fraction was subjected to N-terminal amino acid sequence analysis as described before. The major sequence found was that of natural interferon D. The first 8 N-terminal amino acids of the protein were: cys-asp-leu-pro-glu-thr-his-ser.

Additional Explanatory Notes re Figures

FIG. 2

Localization of homology between the α-factor probes and the DNA fragments from p51 (a) and p52 (b) recombinant plasmids. The two plasmids were digested with different restriction endonucleases and then electrophoresed on a one percent agarose gel. The DNA fragments were transferred to nitrocellulose paper and hybridized to $^{32}$P-labeled probes. Panel A: Ethidium bromide stained gel. Panel B: Southern blot. Lanes: 1, EcoRI; 2, SalI; 3, HindIII; 4, BamHI; 5, PstI. The arrows indicate the two DNA fragments that were subcloned. The size standards were derived from lambda, YRp7, or pBR322 DNA.

FIG. 3

Nucleotide sequence of $MF\alpha_1$ gene and its nontranslated 5' and 3' flanking regions. The predicted amino acids sequence of the pheromone precursor is also shown. The numbers above and below the sequence denote the positions of amino acids and nucleotides, respectively. The four copies of the α-factor sequences are included in the boxed areas. The asterisks indicate differences in the nucleotide sequence in one or more copies of the α-factor coding regions. Three potential N-glycosylation recognition sites are indicated by bars. This gene corresponds to the gene reported by Kurjan, et al. (44).

FIG. 4

Nucleotide sequence of MFα2 gene and its nontranslated 5' and 3' flanking regions. The underlined amino acids indicate differences between the two pheromone copies encoded by the MFα2 gene. See FIG. 3 for other details.

FIG. 5

Joining of the $IFN-\alpha_1$ gene with the α-factor promoter and the α-factor presequence. Since, as shown in FIG. 3, the 1.8 kbp EcoRI fragment contained the promoter, the entire DNA sequence 5' to the sequences coding for the mature α-factor was joined to the modified $IFN-\alpha_1$ gene such that the α-factor presequence and the $IFN-\alpha_1$ protein would be synthesized as a single precursor protein using the α-factor promoter.

FIG. 7

The protein and DNA sequence at the junction of α-factor "prepro" and the modified $IFN-\alpha_1$ genes. The XbaI and EcoRI sites at the junction are indicated.

FIG. 8

Cellular and medium $IFN-\alpha_1$ levels during fermentation. At various time intervals 10 ml culture was removed from the fermentor, centrifuged to separate the cells and medium. Cell extracts were prepared as described above. Interferon levels in the medium and the extracts were determined.

FIG. 9

Construction of a yeast/E. coli shuttle vector plasmid for the expression of heterologous genes using the α-factor promoter and signal sequences. The 1.12 kbp EcoRI fragment containing the promoter and signal sequence was isolated from p58 and was inserted into the EcoRI site of YEp9T.

FIG. 10

Assembly of plasmid p68 for expression and secretion of tissue plasminogen activator.

FIG. 11

Scheme for in vitro deletion mutagenesis. The 24 mucleotides that were deleted at the junction of MF21 "pre-pro" sequence and the modified IFN-α1 gene are shown as a loop in the figure.

FIG. 12

Comparison of amino acid sequences of the putative α-factor precursors encoded by MFα1 and MFα2 genes. Various gaps were created to align the sequences with maximum homology.

BIBLIOGRAPHY

1. Novick, et al., *Cell* 21, 205 (1980).
2. Duntze, et al., *Science* 168, 1472 (1970).
3. Woods, et al., *J. Gen. Microbiol.* 51, 115 (1968).
4. Cabib, et al., *J. Bacteriology* 124, 1586 (1975).
5. Farkas, *Microbiol. Rev* 43, 117 (1979).
6. Moor, Arch. *Mikrobiol.* 57, 135(1967).
7. Goeddel, et al., *Nature* 287, 411 (1980).
8. Goeddel, et al., *Nature* 290, 20 (1981).
9. Yelverton, et al., *Nucleic Acids Research* 9, 731 (1981).
10. Goeddel, et al., *Nucleic Acids Research* 8, 4057 (1980).
11. Wetzel, *American Scientist* 68, 664 (1980).
12. Wetzel, et al., *Biochemistry* 19, 6096 (1980).
13. Davis, et al., *Proc. Natl. Acad. Sci.* (USA) 78, 5376 (1981).
14. Hitzeman, et al., *Nature* 293, 717 (1981).
15. Kleid, et al., *Science* 214, 1125 (1981).
16. Lawn, et al., *Nucleic Acids Res.* 9, 6103 (1981).
17. Weck, et al., *Nucleic Acids Res.* 9, 6153 (1981).
18. Stotlzer, et al., *Eur. J. Biochem.* 65, 257–262 (1976).
19. Stotlzer, et al., *Eur. J. Biochem.* 69, 397–400 (1976).
20. Birnboim, H. C., et al., *Nucleic Acids Research* 7, 1513 (1979).
21. Hinnen, A., et al., *Proc. Natl. Acad. Sci.* (USA) 75, 1929 (1978).
22. Backman, et al., *Proc. Natl. Acad. Sci* (USA) 73, 4174-(1976).
23. Mandel, et al., *J. Mol. Biol.* 53, 159 (1970).
24. Beggs, *Nature* 275, 104 (1978).
25. Miller, J. H., *Experiments in Molecular Genetics*, pp. 431, Cold Spring Harbor Laboratory, Cold Spring Harbor, N.Y.
26. Stewart, W. E. II *The Interferon System* (Springer, N.Y., 1979).
27. P. Edman, G. Begg, "A Protein Sequencer" *Eur. J. Biochem.* 1, 80 (1967).
28. Tarr, G. E., et al., *Anal. Biochem.* 84, 622 (1978).
29. Clernell, et al., *Biochemistry* 9, 4428 (1970).
30. Holland, et al., *J. Biol. Chem.* 254, 9839 (1979).
31. Holland, et al., *J. Biol. Chem.* 255, 2596 (1980).
32. Struhl, et al., *Proc. Natl. Acad. Sci. USA* 76, 1035 (1979).
33. Bolivar, F., et al., *Gene* 2, 950113 (1977).
34. Stinchcomb, D. T., et al., *Nature* 282, 39 (1979).
35. Kingsman, et al., *J. Gene* 7, 141 (1979).
36. Tschumper, G., et al., *Gene* 10, (1980).
37. Hartley, J. L. et al., J. E. *Nature* 286, 860 (1980).

38. Grunstein, et al., *Proc. Natl. Acad. Sci. USA* 72, 3961 (1975).
39. Messing, et al., *Nucleic Acids Research* 9, 309 (1981).
40. Maxam, A. M., and Gilbert, W., *Methods in Enzymol.* 65, 490 (1980).
41. Crea, R. and Horn, T. *Nucleic Acids Res.* 8, 2331 (1980).
42. Southern, *J. Mol. Biol.* 98, 503 (1975).
43. Broach, et al., *Gene* 10, 157 (1979).
44. Kurjan, et al., *Cell* 30, 933 (1982).
45. Smith, *Methods Enzymol.* 65, 499 (1980).
46. Bennetzen, J. L., et al., *J. Biol. Chem.* 257, 3026 (1982).
47. Sanger, et al., *Proc. Natl. Acad. Sci. USA* 74, 5463 (1977).
48. Mains, et al., *Proc. Natl. Acad. Sci. USA* 74, 3014 (1977).
49. Nakanishi, et al., *Nature* 278, 423 (1979).
50. Comb, et al., *Nature* 295, 663 (1982).
51. Gubler, et al., *Nature* 295, 206 (1982).
52. Noda, et al., *Nature* 295, 202 (1982).
53. Kokidani, et al., *Nature* 298, 245 (1982).
54. Barnes, et al., Berkeley Workshop on Recent Advances In Yeast Molecular Biology (1982): Recombinant DNA, Esposito, et al. Eds., pp. 295–305, Lawrence Radiation Laboratory, University of California, Berkeley, Calif.
55. Julius, et al., *Cell* 32, 839 (1982).
56. Kreil, et al., *Eur. J. Biochem.* 111, 49 (1980).
57. Hoffman, et al., *EMBO J.* 2, 111 (1983).
58. Weck, et al., *Nuc. Acid Res.* 9, 6153 (1981).
59. Hitzeman et al., *Science* 219, 620 (1983).
60. Pennica, et al., *Nature* 301, 214 (1983).
61. Messig, J. (1981) pp. 143–153 in Third Cleveland Symposium on Macronolecules: Recombinant DNA, Ed. A. Walton, Elsevier, Amsterdam.
62. Messig, J., *Recombinant DNA Technical Bulletin* 2, 43 (1979).

The invention claimed is:

1. A process for obtaining a protein heterologous to yeast as a product of yeast expression, which process comprises:
    (a) transforming a yeast organism with an expression vehicle comprising a promoter sequence for yeast alpha factor operably connected to a DNA sequence encoding a pre-pro peptide of yeast alpha factor operably connected in translation reading frame to a DNA sequence encoding a protein heterologous to the yeast organism;
    (b) culturing the transformed organism; and
    (c) recovering the protein from the culture,
    wherein the heterologous protein is selected from the group consisting of interferon, serum albumin, tissue plasminogen activator, rennin and insulin-like growth factor.

2. A process for obtaining a protein heterologous to yeast as a product of yeast expression, processing and secretion, which process comprises:
    (a) transforming a yeast organism with an expression vehicle comprising a promoter sequence for yeast alpha factor operably connected to a DNA sequence encoding a pre-pro peptide of yeast alpha factor operably connected in translation reading frame to a DNA sequence encoding a protein heterologous to the yeast organism;
    (b) culturing the transformed organism; and
    (c) recovering the protein from the culture,
    wherein the heterologous protein is selected from the group consisting of interferon, serum albumin, tissue plasminogen activator, rennin and insulin-like growth factor.

3. A process for secreting a protein heterologous to yeast into the supporting medium, which process comprises:
    (a) transforming a yeast organism with an expression vehicle comprising a promoter sequence for yeast alpha factor operably connected to a DNA sequence encoding a pre-pro peptide of yeast alpha factor operably connected in translation reading frame to a DNA sequence encoding a protein heterologous to the yeast organism;
    (b) culturing the transformed organism; and
    (c) recovering the protein from the cultures
    wherein the heterologous protein is selected from the group consisting of interferon, serum albumin, tissue plasminogen activator, rennin and insulin-like growth factor.

4. A yeast expression vehicle comprising a promoter sequence for yeast alpha factor operably connected to a DNA sequence encoding a pre-pro peptide of yeast alpha factor operably connected in translation reading frame to a DNA sequence encoding a protein heterologous to the yeast organism.

5. A yeast organism transformed by the expression vehicle of claim 4.

6. The process of claim 1, wherein the heterologous protein is human interferon.

7. The process of claim 1, wherein the heterologous protein is bovine interferon.

* * * * *